(12) United States Patent
Mosca (10) Patent No.: US 7,101,704 B1
(45) Date of Patent: Sep. 5, 2006

(54) ANTIGEN PRESENTING MESENCHYMAL STEM CELLS

(75) Inventor: Joseph Mosca, Ellicott City, MD (US)

(73) Assignee: Osiris Therapeutics, Inc., Baltimore, MD (US)

( * ) Notice: Subject to any disclaimer, the term of this patent is extended or adjusted under 35 U.S.C. 154(b) by 1002 days.

(21) Appl. No.: 09/638,358

(22) Filed: Aug. 15, 2000

Related U.S. Application Data (62) Division of application No. 09/157,008, filed on Sep. 18, 1998, now Pat. No. 6,149,906.

(60) Provisional application No. 60/059,690, filed on Sep. 20, 1997.

(51) Int. Cl.
*C12N 5/10* (2006.01)
*C12N 5/06* (2006.01)
*C12N 15/63* (2006.01)
*A61K 48/00* (2006.01)

(52) U.S. Cl. ............... 435/325; 435/455; 424/93.2; 424/93.21

(58) Field of Classification Search ............. 435/325, 435/455; 424/93.2, 93.21
See application file for complete search history.

(56) References Cited

U.S. PATENT DOCUMENTS 5,591,625 A * 1/1997 Gerson et al. ............ 435/240.2
5,962,320 A * 10/1999 Robinson .................. 435/366

OTHER PUBLICATIONS

Bachmann et. al.; In vivo versus in vitro assays for assessment of T- and B- cell function, 1994, Current Opinion in Immunology 6: 320-326.*

Yasutomi et. al.; A Vaccine-Elicited, Single Viral Epitope-Specific Cytotoxic T Lymphocyte Response . . . Virus Challenge, 1995. Journal of Virology: 2279-2284.*
Ross et. al.; Gene Therapy in the United States: A Five-Year Status Report, 1996, Human Gene Therapy 7: 1781-.*
Orkin et. al.; Report and Recommendations of the Panel to Assess the NIH Investment in Research on Gene Therapy, 1995.*
Melian et al. (1996) Current Opin. Immunol., vol. 8, 82-88.*
Krampera et al. (2003) Blood, vol. 101, No. 9, 3722-3729.*

* cited by examiner

*Primary Examiner*—Anne M. Wehbé
(74) *Attorney, Agent, or Firm*—Elliot M. Olstein; Raymond J. Lillie (57) ABSTRACT

Disclosed is a mesenchymal stem cell and/or cell of the adipocyte lineage that (i) has been modified to have at least one exogenous antigen bound to at least one primary surface molecule of said cell such that said at least one antigen can initiate an immune response and (ii) also expresses at least one co-stimulatory molecule. The antigen is preferably a protein, polypeptide, lipid or glycolipid. The primary surface molecule is MHC I, MHC II or CD1. Also disclosed is a method for stimulating presentation of at least one exogenous antigen fragment on a mesenchymal stem cell primary surface molecule by contacting a mesenchymal stem cell that is capable of expressing at least one co-stimulatory molecule with (i) an exogenous antigen or (ii) genetic material that codes for the exogenous antigen which the mesenchymal stem cell processes into at least one antigen fragment. The method can further include contacting the mesenchymal stem cell with interferon-γ. Also disclosed are a method for determining the state of activation of a T lymphocyte population and a method for the treatment or prevention of a disease in an animal.

18 Claims, 7 Drawing Sheets

Antigen Presentation By hMSCs

Figure 3

Expression of Class II and B7
Co-stimulatory Molecules By hMSCs

Figure 4

Antigen Presentation By B7-Transduced hMSCs

Map of aP2 Promoter and Reporter Constructs

FIGURE 7

Differentiation-dependent expression of proteins in hMSC: Expression of GFP-reporter by adipose-specific promoters

FIGURE 8

ANTIGEN PRESENTING MESENCHYMAL STEM CELLS

This is a Divisional of application Ser. No. 09/157,008, filed Sep. 18, 1998, now issued as U.S. Pat. No. 6,149,906, which is based on Provisional Application Ser. No. 60/059,690, filed Sep. 20, 1997.

This invention relates to the field of antigen presentation for the activation of T-lymphocytes and the resultant induction of antigen-specific immune responses.

BACKGROUND OF THE INVENTION

Antigens are processed by antigen-presenting cells. In order to trigger an efficient immune response, antigens must first be processed by an antigen-presenting cell (APC) that degrades the antigen and "presents" the resulting antigen fragments to other cells involved in the immune response. Macrophages are among the most commonly encountered type of APC; other examples include dendritic cells in the spleen and Kupffer cells in the liver. Macrophages readily engulf foreign particles and cells by the process of phagocytosis. Although all macrophages are avid phagocytes, only some can process foreign antigens in a way that stimulates an immune response. The macrophages that perform this function carry specialized plasma membrane glycoproteins called major histocompatibility complex (MHC) molecules. In man the MHC is known as HLA. MHC molecules reside only on the surfaces of cells involved in immune responses.

The processing of foreign antigens by macrophages and other APCs involves four main stages. First, antigens are taken into the cell by a relatively nonspecific form of endocytosis that brings all molecules dissolved in the extracellular fluid into the cell. Next, the internalized endocytic vesicles fuse with lysosomes, whose hydrolytic enzymes degrade the foreign antigens into small fragments. In the case of ingested protein antigens, the process yields peptide fragments about 10–20 amino acids long. Third, the resulting fragments become bound to MHC class II molecules, which possess an antigen-binding cleft that is specifically designed to bind antigen fragments. Finally, the foreign antigen-MHC II complex is transported to the cell surface for "presentation" to other cells of the immune system. The importance of the preceding pathway has been demonstrated by treating cells with inhibitors that block endocytosis or the lysosomal degradation of antigens; under such conditions, an immune response is inhibited.

The pathway that was just described is used in the processing of exogenous antigens (i.e. antigens that have been taken up from outside the cell. Immune responses can also be triggered by endogenous antigens that originate within the cells of the host organism. For example, cells that have become infected by a virus usually manufacture foreign proteins encoded by viral genes. Fragments derived from the viral proteins become bound to a different type of MHC molecule called an MHC class I molecule. Peptide antigens destined to bind to MHC class I molecules are produced by protein cleavage in the cytosol and are then transported into the lumen of the endothelial reticulum, where the fragments bind to class I molecules associated with the endothelial reticulum membrane. The resulting antigen-MHC I complex is then transported to the cell surface, where its presence can trigger an immune response against the infected cell. (Peptide fragments derived from a cell's own normal proteins can also bind to MHC class I molecules and be presented at the cell surface, but such "self" antigen-MHC complexes do not usually elicit an immune response.)

Activation of naive T-cells requires recognition of a foreign antigenic fragment bound to a self MHC molecule but this is not on its own sufficient for activation. It also requires the simultaneous delivery of a co-stimulatory signal by a specialized antigen-presenting cell. It has been believed that only professional antigen-presenting cells (APCs) are able to express both classes of MHC molecules as well as the co-stimulatory surface molecules that drive the clonal expansion of naive T-cells and their differentiation into armed effector T-cells. The activation of naive T-cells on initial encounter with antigen on the surface of a professional antigen-presenting cell is often called priming, to distinguish it from the responses of armed effector T-cells to antigen on their target cells, and the responses of primed memory T-cells.

Effector T-cells are triggered when their antigen-specific receptors (T cell receptors) and either the CD4 or the CD8 co-receptors bind to peptide-MHC complexes. But ligation of the T-cell receptor and co-receptor does not, on its own, stimulate naive T-cells to proliferate and differentiate into armed effector T-cells. The antigen-specific clonal expansion of naive T-cells requires a second, co-stimulatory, signal which is delivered by the same antigen-presenting cell on which the T-cell recognizes its specific antigen.

The best characterized co-stimulatory molecules on antigen-presenting cells are the structurally related glycoproteins B7-1 and B7-2. These are homodimeric members of the immunoglobulin superfamily found exclusively on the surface of cells capable of stimulating T-cell growth. The receptor for B7 molecules on the T-cell is CD28, yet another member of the immunoglobulin superfamily. Ligation of CD28 by B7-1 or B7-2 or by anti-CD28 antibodies will co-stimulate the growth of naive T-cells, while antibodies to the B7 molecules, which inhibit their binding to CD28, inhibit T-cell responses.

On naive T-cells, CD28 is the only receptor for B7-1 and B7-2. Once T-cells are activated, however, they express an additional receptor called CTLA-4, which binds B7 molecules with a higher affinity than does CD28. CTLA-4 closely resembles CD28 in sequence, and the two molecules are encoded by closely linked genes. CTLA-4 binds more avidly than CD28 but appears to play a negative role in the activation of the T-cell expressing it. The activated progeny of a naive T-cell become less sensitive to stimulation by antigen than the naive T-cells. This may help to limit the early proliferative response of the T-cells to antigen and B7 molecules on the surface of antigen-presenting cells. Although other molecules have been reported to co-stimulate naive T-cells, to date only B7-1 and B7-2 binding to CD28 has been shown definitively to provide co-stimulatory signals in normal immune responses.

The requirement for simultaneous delivery of antigen-specific and co-stimulatory signals in the activation of naive T-cells means that only professional antigen-presenting cells can initiate T-cell responses. This is important because not all potentially self-reactive T-cells are deleted in the thymus: peptides derived from proteins made only in specialized cells in the peripheral tissues may not be encountered during the negative selection of thymocytes. Self tolerance could be broken if naive, autoreactive T-cells could recognize self antigens on tissue cells and then be co-stimulated by a professional antigen-presenting cell, either locally or at a distant site. Thus, the requirement that the same cell presents both the specific antigen and the co-stimulatory signal plays an important part in preventing destructive immune responses to self tissues. Indeed, antigen binding to the T-cell receptor in the absence of co-stimulation not only fails to activate the cell but also leads to a state called anergy, in which the T-cell becomes refractory to activation.

For many years, immunologists studying how the immune system recognizes foreign molecules have focused on the molecular mechanisms by which T-cells recognize peptide antigens. Zeng et al., Science. 277:339 (1997) present the three-dimensional structure of murine CD1d, a representative of a family of conserved mammalian proteins that are somewhat related to MHC molecules. This structure reinforces the view that CD1 proteins bind and present antigen in a way that allows T-cells to be activated by lipid and glycolipid antigens.

The CD1 genes are located on a different chromosome than the MHC in humans. These are nonpolymorphic proteins with only about 30% homology to MHC class I or II molecules. Despite this marked divergence from MHC structure, a role for CD1 in antigen presentation was shown by the finding that CD1 expression on antigen-presenting cells was required for the responses of certain T-cell clones to *Mycobacterium tuberculosis*. Further studies in this system led to the finding that the mycobacterial antigens recognized by CD1 restricted T-cells are not peptides, but instead are lipids (mycolic acids) and glycolipids found in the cell walls of these bacteria.

Mesenchymal stem cells are the formative pluripotential blast cells found inter alia in bone marrow, blood, dermis and periosteum that are capable of differentiating into any of the specific types of mesenchymal or connective tissues (i.e. the tissues of the body that support the specialized elements; particularly adipose, osseous, cartilaginous, elastic, and fibrous connective tissues) depending upon various influences from bioactive factors, such as cytokines. Although these cells are normally present at very low frequencies in bone marrow, a process has been discovered for isolating, purifying, and greatly replicating these cells in culture, i.e. in vitro. See, Caplan and Haynesworth, U.S. Pat. No. 5,486,359.

In order to isolate human mesenchymal stem cells, it is necessary to isolate rare pluripotent mesenchymal stem cells from other cells in the bone marrow or other MSC source. Bone marrow cells may be obtained from iliac crest, femora, tibiae, spine, rib or other medullary spaces. Other sources of human mesenchymal stem cells include embryonic yolk sac, placenta, umbilical cord, fetal and adolescent skin, and blood.

Isolated human mesenchymal stem cell compositions serve as the progenitors for multiple mesenchymal cell lineages including bone, cartilage, ligament, tendon, adipose, muscle, stroma, dermis and other connective tissues. These isolated mesenchymal cell populations have the ability to expand in culture without differentiating, and have the ability to differentiate into specific mesenchymal lineages when either induced in vitro or placed in vivo at the site of damaged tissue. To date, they have conventionally been associated with their usefulness in connective tissue repair.

SUMMARY OF THE INVENTION

In accordance with one aspect, the present invention is directed to inducing an antigen specific T cell mediated immune response by using adipocytes and/or mesenchymal stem cells as an antigen presenting cell(s). The T-cell response is preferably a cytotoxic T-cell (CTL) response. The mesenchymal stem cells and/or adipocytes can be autologous, allogeneic or xenogeneic, although autologous is usually preferred, to any intended recipient.

Mesenchymal stem cells (MSCs) derived from bone marrow or other sources are ideal candidates for utilization as non-professional APCs. Large numbers of these cells can be produced from relatively small amounts of bone marrow (up to 20 billion cells from 40 ml bone marrow). The cells are amenable to genetic engineering, and the cells can be differentiated into various tissues, potentially allowing tissue-specific antigen presentation. These are distinct advantages over professional APCs which can not be expanded into large populations and are difficult to engineer.

In one aspect the invention provides a mesenchymal stem cell and/or adipocytes preferably a human mesenchymal stem cell and/or adipocytes that has been modified to have at least one exogenous antigen fragment (the antigen can be a protein, polypeptide, lipid or glycolipid) bound to a primary surface molecule of said cell such that said at least one antigen fragment is presented to initiate an immune response. In one embodiment of this aspect, the mesenchymal stem cell and/or adipocyte is contacted with at least one antigen or the appropriate fragment (antigen-pulsing) which the mesenchymal stem cell and/or adipocyte processes into an antigen fragment (peptide) which fragment is presented on the surface. In another embodiment, the mesenchymal stem cell and/or adipocyte contains exogenous genetic material that codes for at least one exogenous antigenic polypeptide, which the mesenchymal stem cell and/or adipocyte expresses, processes into an antigen fragment and then presents to initiate an immune response, e.g. T cell activation. Preferably, this exogenous genetic material is in one or more expression vectors. Further, the mesenchymal stem cell and/or adipocyte also expresses at least one co-stimulatory molecule. Therefore in this aspect, the mesenchymal stem cell and/or adipocyte (to the extent that a co-stimulatory molecule is not present) is provided with exogenous genetic material that codes for at least one co-stimulatory molecule. Preferably this exogenous genetic material is in an expression vector. The primary surface molecule is MHC II, MHC I or CD1, preferable MHC II. The co-stimulatory molecule is preferably selected from the group consisting of B7-1 and B7-2.

In another aspect the invention provides a mesenchymal stem cell, preferably a human mesenchymal stem cell, that (i) has been modified to have at least one exogenous antigen fragment (the antigen can be a protein, polypeptide, lipid or glycolipid) bound to a primary surface molecule of said cell such that said at least one antigen fragment is presented to initiate an immune response and which is induced to differentiate into cells of the adipocytic lineage. It has been discovered that adipocytes express MHC class II molecules. Thus, adipocytes can be used for antigen presentation.

In one embodiment of this aspect, prior to differentiation into the adipocyte lineage, the mesenchymal stem cell is contacted with at least one antigen (antigen-pulsing) which the mesenchymal stem cell processes into an antigen fragment that is presented on the cell surface. In another embodiment, the mesenchymal stem cell contains exogenous genetic material that codes for at least one exogenous antigenic polypeptide, which the mesenchymal stem cell expresses, processes into an antigen fragment and then presents to initiate an immune response, e.g. T cell activation. Preferably, this exogenous genetic material is in one or more expression vectors. The mesenchymal stem cell also expresses at least one co-stimulatory molecule which co-stimulatory molecule is generally produced by providing the mesenchymal stem cell with exogenous genetic material that expresses the co-stimulatory molecule. The modified mesenchymal stem cell is then induced to differentiate into the adipocyte lineage.

In another embodiment, the mesenchymal stem cells are first induced to differentiate into the adipocyte lineage. The mesenchymal stem cells may preferably be modified to contain co-stimulatory molecules prior to induction of differentiation. After differentiation, the adipocytes are provided with antigen which the adipocytes process into antigen fragments.

In a still further aspect, adipocytes are contacted with antigen which the adipocyte processes into an antigen fragment. In one embodiment, the adipocyte is also modified to contain genetic material that codes for at least one co-stimulatory molecule such as B7-1 or B7-2.

In another aspect the invention provides a method for stimulating presentation of at least one exogenous antigen fragment on a mesenchymal stem cell primary surface molecule, which method comprises providing a mesenchymal stem cell that is capable of expressing at least one co-stimulatory molecule with (i) an exogenous antigen or appropriate fragment thereof or (ii) genetic material that codes for the exogenous antigen or appropriate fragment which the mesenchymal stem cell processes into at least one antigen fragment that is presented on the cell surface. The method can further include contacting the mesenchymal stem cell with at least one cytokine, such as interferon-γ.

In a further aspect the invention provides a method for stimulating presentation of at least one antigen on a cell of the adipocyte lineage wherein a mesenchymal stem cell is caused to differentiate into the adipocyte lineage, which method comprises contacting a mesenchymal stem cell that is preferably capable of expressing at least one co-stimulatory molecule with (i) an exogenous antigen or (ii) genetic material that codes for the exogenous antigen which the mesenchymal stem cell processes into at least one antigen fragment. The method can further include contacting the mesenchymal stem cell with at least one cytokine, such as interferon-γ. The mesenchymal stem cell is then caused to differentiate into the adipocyte lineage and the cell of the adipocyte lineage functions to present such antigen to the immune system to induce a T cell response.

In another embodiment, after the MSC is caused to differentiate into the adipocyte lineage, cells of the adipocyte lineage are provided with the antigen that is to be presented to the immune system and to the extent necessary, such cells are provided with a co-stimulatory molecule.

In another aspect the invention provides a method of activating or priming a naive T-lymphocyte to an antigen which comprises contacting the T-lymphocyte with a mesenchymal stem cell and/or cell of the adipocyte lineage which presents an antigen fragment and also expresses at least one co-stimulatory molecule. Preferably, the T-lymphocyte is contacted with the mesenchymal stem cell and/or cell of the adipocyte lineage in the presence of at least one cytokine, such as interferon-γ. The primed T-cell may be used to treat or prevent a disease that results from the antigenic source against which the T-cell has been primed.

In another aspect the invention provides a mesenchymal stem cell and/or cell of the adipocyte lineage which expresses at least one soluble or membrane bound exogenous antigen or antigen fragment and also expresses a co-stimulatory molecule. Thus, the mesenchymal stem cell and/or cells of the adipocyte lineage can make the antigen or antigen fragment available to "professional" antigen presenting cells for T-cell activation. In one embodiment of this aspect, the mesenchymal stem cell and/or cells of the adipocyte lineage has been contacted with at least one exogenous antigen which the mesenchymal stem cell processes into at least one antigen fragment. In another embodiment, the human mesenchymal stem cell and/or cells of the adipocyte lineage contains exogenous genetic material that codes for the at least one exogenous antigen which the mesenchymal stem cell processes into at least one antigen fragment. Preferably this exogenous genetic material is in an expression vector. Further, the mesenchymal stem cell and/or cells of the adipocyte lineage can also contain exogenous genetic material that codes for at least one co-stimulatory molecule. Preferably, this exogenous genetic material is also in an expression vector.

In another aspect, the invention further provides a method for determining the state of activation of a T cell population to a particular antigen by contacting the T cell population with the mesenchymal stem cells of the invention and observing any change in an indicator of the state of activation (e.g., tritiated thymidine uptake, T cell interferon production or expression of T cell surface activation markers).

The invention further relates to the treatment or prevention of a disease in an animal, which may be a human or non-human, by administering to the animal mesenchymal stem cells and/or cells of the adipocyte lineage that (i) have been modified to have at least one exogenous antigen fragment (the antigen can be a protein, polypeptide, lipid or glycolipid) bound to a primary surface molecule of said cell such that said at least one antigen fragment can be presented to initiate an immune response and (ii) also expresses at least one co-stimulatory molecule. In one embodiment of this aspect, the mesenchymal stem cell and/or cells of the adipocyte lineage is contacted with at least one antigen (or appropriate fragment thereof) which the mesenchymal stem cell processes into an antigen fragment that is presented on the cell surface. In another embodiment, the mesenchymal stem cell and/or cells of the adipocyte lineage contains exogenous genetic material that codes for at least one exogenous antigenic polypeptide which the mesenchymal stem cell and/or cells of the adipocyte lineage processes into an antigen fragment that is presented on the cell surface. Such methods of prevention and/or treatment have application with respect to various diseases (whether a viral, bacterial, fungal or other origin), toxin exposure (e.g. botulism toxin, ebola or hantavirus) or antigens of plant origin (e.g. poison ivy, poison sumac) and the like.

BRIEF DESCRIPTION OF THE DRAWINGS

The invention is further described by the accompanying drawings and the description thereof herein, although neither is a limitation of the scope of the invention.

DETAILED DESCRIPTION OF THE PREFERRED EMBODIMENTS

The present invention relates to the use of MSCs and/or cells of the adipocyte lineage as antigen presenting cells for the activation of T cell responses, and in an in vitro method for assessing immune responsiveness of both unprimed and primed individuals to potentially immunogenic epitopes using MSCs or cells of the adipocyte lineage as APC, and CD4$^+$ and/or CD8$^+$ T cells as responders.

In the embodiments in which the mesenchymal stem cells are caused or induced to differentiate into the adipocyte lineage, such induction may be effected as described in co-pending U.S. application Ser. No. 08/700,753.

In a preferred embodiment, the cells of the adipocyte lineage used in the invention are produced in vitro from mesenchymal stem cells. In accordance with the invention, the adipocytes may be obtained by collecting and culturing cells that are committed to the adipocyte lineage. Such cells are then used as antigen presenting cells in accordance with the invention.

The invention provides for use of MSCs or cells of the adipocyte lineage to present a relevant antigen as an immunoprophylactic or immunotherapy to treat, for example, cancer, exposure to toxins, infectious diseases and as an alternative to conventional drug and antibiotic therapies on which resistance has developed. Pursuant to the present invention, molecules have been expressed and/or induced on the surface of the MSC and/or cells of the adipocyte lineage in order to either present transduced antigen(s) directly to the immune system, or to produce and secrete antigens that will be picked up by "professional" APCs, such as dendritic cells and macrophages, for presentation to lymphoid cells. The minimum requirements of an APC for activation of T-lymphocytes are to degrade complex protein antigens into antigen fragments, to present these antigen fragments on MSC and/or cells of the adipocyte lineage by way of primary surface molecules and to express co-stimulatory molecules, like B7-1 and B7-2.

The term "isolated" means altered "by the hand of man" from its natural state; i.e., if it occurs in nature, it has been changed or removed from its original environment, or both. With respect to a human mesenchymal stem cell (hMSC), it is isolated when it has been removed from a donor's body. In one contemplated sense, this is true even when the hMSC is still in a mixed cell population. In another contemplated sense, the hMSC is treated to separate it from other types of cells, such as differentiated mesenchymal cells or hematopoietic cells, such as are found, for example, in bone marrow. In another contemplated sense it can refer to MSC enrichment and culture expansions. Such procedures are fully disclosed in Caplan and Haynesworth, U.S. Pat. No. 5,486,359.

For example, a naturally occurring polynucleotide or polypeptide naturally present in a living animal in its natural state is not "isolated", but the same polynucleotide or polypeptide separated from the coexisting materials of its natural state is "isolated", as the term is employed herein. For example, with respect to polynucleotides, the term isolated means that it is separated from the nucleic acid and cell in which it naturally occurs.

As part of or following isolation, such polynucleotides can be joined to other polynucleotides, such as DNAs, for mutagenesis, to form fusion proteins, and for propagation or expression in a host (i.e. hMSCs), for instance. The isolated polynucleotides, alone or joined to other polynucleotides such as vectors, can be introduced into host cells, in culture or in whole organisms. Introduced into host cells in culture or in whole organisms, such polynucleotides still would be isolated, as the term is used herein, because they would not be in their naturally occurring form or environment. Similarly, the polynucleotides and polypeptides may occur in a composition, such as a media formulation (solutions for introduction of polynucleotides or polypeptides, for example, into cells or compositions or solutions for chemical or enzymatic reactions which are not naturally occurring compositions) and, therein remain isolated polynucleotides or polypeptides within the meaning of that term as it is employed herein.

The term "ligation" refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y. (1989).

The term "gene" means the segment of DNA involved in producing a polypeptide chain; it includes regions preceding and following the coding region (leader and trailer) as well as intervening sequences (introns) between individual coding segments (exons).

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein.

"Recombinant" antigens refer to antigens produced by recombinant DNA techniques; i.e., produced from cells transformed by an exogenous DNA construct encoding the desired enzyme. "Synthetic" antigens are those prepared by chemical synthesis.

A DNA "coding sequence of" or a "nucleotide sequence encoding" a particular enzyme, is a DNA sequence which is transcribed and translated into an enzyme when placed under the control of appropriate regulatory sequences.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

The hMSCs and/or cells of the adipocyte lineage used in the invention can be genetically engineered (transduced or transformed or transfected) with vectors which may be, for example, an expression vector. The vector may be, for example, in the form of a plasmid, a virus, etc. The engineered hMSCs can be cultured in conventional nutrient media modified as appropriate for activating promoters, selecting transformants or amplifying exogenous genes therein. The culture conditions, such as temperature, pH and the like, can be those previously used. See, for example, Gerson et al., U.S. Pat. No. 5,591,625.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR and other promoters known to control expression of genes in eukaryotic cells or their viruses. The expression vector also contains a ribosome binding site for translation initiation and a transcription terminator. The vector may also include appropriate sequences for amplifying expression. In addition, the expression vectors preferably contain one or more selectable marker genes to provide a phenotypic trait for selection of transformed host cells such as dihydrofolate reductase or neomycin resistance.

Unless otherwise stated, genetic manipulations were performed as described in Sambrook and Maniatis, Molecular Cloning: A Laboratory Manual, Cold Spring Harbor Laboratory, 1989.

The potent accessory cell function of the MSCs and/or cells of the adipocyte lineage used in the invention provides an antigen presentation system for virtually any antigenic epitopes which T and B cells are capable of recognizing through their specific receptors. MSCs and/or cells of the adipocyte lineage can present both complex protein antigens and small peptides to CD4$^+$ T cells as well to as CD8$^+$ CTL. T cell activation is manifested by T cell proliferation and/or cytotoxicity in response to antigen. Hence, MSCs and/or cells of the adipocyte lineage may be used for presenting antigens encoded by infectious agents such as viruses and microorganisms as well as rumor antigens expressed by cancer cells.

Infectious agents against which the present invention may be applicable in the induction of an immune response include, but are not limited to, bacteria, parasites, fungi, and viruses. The multitudes of antigens encoded by these agents, which may be processed and presented by MSCs and/or cells of the adipocyte lineage include but are not limited to, external surface proteins, and structural proteins including internal enzymes. A variety of other infectious agents including hepatitis B virus, hepatitis C virus, cytomegalovirus, herpes simplex virus, varicella zoster, and Mycohacteria species are encompassed within the scope of the invention.

A large number of human tumor-associated antigens have been identified by monoclonal antibodies. Although these cellular antigens are selectively expressed in higher quantities by certain tumor cells, it has not been established that they naturally elicit an immune response in cancer patients or can be used effectively to induce such a response. Progress in this area is, in part, hampered by the lack of an adequate in vitro system for analyzing human anti-tumor immune responses, particularly T cell-mediated responses.

Unlike animal tumor models in which tumor-reactive T and B cells can be induced through hyperimmunization with tumor cells or tumor antigens, human tumor cells or oncogenic proteins may not be injected into humans for stimulating tumor-reactive T cells due to ethical limitations. Thus, most human studies have utilized lymphocytes obtained from cancer patients whose cells presumably have been exposed to antigens expressed by their autologous tumor cells in vivo.

However, it has been shown in some systems that tumor development is accompanied by a down-regulation of tumor specific immune responsiveness mediated by suppressor cells, and if so, T cells isolated from cancer patients may have already come under the influence of such suppression in vivo so as to not function in a manner similar to that of T cells obtained from tumor-immune hosts. Moreover, these attempts to activate human tumor-reactive T cells have generally used monocytes as APCs, which are shown herein to be much less effective APCs than MSCs, especially if the T cells have not been primed adequately in vivo against the tumor antigens. Alternatively, cytotoxic lymphocytes have been directly activated by use of high doses of lymphokines, such as IL-2, but this approach suffers from a lack of tumor specificity and various toxic side effects.

MSCs described herein may be used for assessing and stimulating human anti-tumor responses, using naive lymphocytes from normal, presumably unsuppressed, individuals or T cells from tumor-bearing patients. The potent accessory cell function of MSCs may be used to present tumor antigens to T cells from cancer patients, whose immune response is apparently inadequate to eliminate the tumors in vivo. The activated T cells can be expanded in vivo. The activated T cells can be expanded in vitro for use in immunotherapy. Whole tumor cells in viable or irradiated form, tumor membrane preparations, and tumor antigens purified from natural sources or expressed as recombinant products may be used to pulse MSCs for presentation to T cells.

Recently, oncogene products have been shown to be capable of inducing murine T cell responses. For example, oncogenic forms of the ras gene product p21, and the fusion product p210 of the bcr-abl gene induce T cell proliferative responses, when used to immunize mice. Thus, oncogenic proteins which are different from their normal cellular counterparts as a result of amino acid substitutions can possess new immunogenic determinants that are recognizable by T cells. For example, one molecule that has been shown to induce cytotoxic T cells to react against murine tumors is p53. It is believed that overexpressing a portion of the p53 wildtype phenotype via MSCs and/or cells of the adipocyte lineage may induce an immune response against the mutated p53 which when expressed allows uncontrolled growth of cells leading to cancerous tumors. It is not necessary that such proteins be expressed naturally on the cell surface, as cytoplasmic and nuclear proteins may be processed, attached to MHC-encoded products intracellularly, and translocated to the cell surface in a complex form. Since oncogene products are expressed in a variety of tumor types including colon cancer, leukemia and lymphoma. MSCs may be used to activate T cells against such cancers. Human T cells, particularly CTL specific for oncogene products, can be induced by MSC presentation, and expanded for the procurement of large numbers of tumor-specific T cells for cellular immunotherapy in vivo.

Bacterial, parasitic, fungal, viral, and tumor antigens of cellular or viral origin can be introduced to MSCs and/or cells of the adipocyte lineage in culture, by the osmotic lysis of pinosomes after pinocytotic uptake or by uptake in antigen-containing liposomes. Antigens can be used as purified naturally occurring whole polypeptides, purified recombinant whole polypeptides, whole organisms or cells in viable or dead forms, protein fragments generated by enzymatic digestion, or synthetic peptides produced by solid phase chemical method. The amount of antigen necessary for pulsing MSCs and/or cells of the adipocyte lineage may vary depending on the nature, size, and purity of the molecules. In general, polypeptides may be used at 1–100 µg/ml, and small peptides at 1–50 βg/ml. Introduction by osmotic lysis of pinosomes requires larger amounts of proteins in the range of 200–500 µg/$10^6$ APC. Alternatively, exogenous genes encoding specific antigens of interest or expression vectors containing such genes or portions thereof may be incorporated into MSCs and/or cells of the adipocyte lineage in expression vectors using conventional methods, including transfection, recombinant vaccinia viruses, adenoviruses, adeno-associated viruses and retroviruses. This approach causes the continual expression of integrated genes, leading to MHC occupancy by the gene products. Any of the above-mentioned methods for introducing exogenous antigens into MSCs and/or cells of the adipocyte lineage as well as any others commonly used by those skilled in the art are hereinafter collectively referred to as pulsing of APC. Antigen pulsing of MSCs and/or cells of the adipocyte lineage may occur prior to co-culture with T cells or antigens may be added to cultures containing both MSCs and/or cells of the adipocyte lineage and T cells at the same time.

A wide variety of uses for this antigen presentation system is contemplated by the invention described herein, including but not limited to, the activation and expansion of antigen-specific T cells in vitro for use in cellular immunotherapy of infectious diseases and cancer, the in vivo administration of antigen-pulsed MSCs and/or cells of the adipocyte lineage as vaccines for priming primary responses or for re-activating secondary immune responses, and the identification of antigenic epitopes for vaccine development.

Among the most advanced approaches to vaccine development has been the use of live cells or organisms for in vivo administration thereby providing a nearly perpetual source of immunizing antigen. A number of bacteria and viruses have been used in an attenuated form to minimize their virulence. In some circumstances such organisms have also been made to contain exogenous or foreign antigens which provide multivalent vaccines. In the ideal situation one would want to be able to use cells that are the least foreign to the intended recipient or patient while they are among the most powerful in providing a broad spectrum of antigens that are expressed in the system that produces or mounts the most effective immune response system. This is a principal advantage provided by the present invention.

Accordingly another aspect is the development and use of vaccines which comprise the mesenchymal stem cells and/or cells of the adipocyte lineage described above in prophylaxis and therapy of disease. Accordingly, the method provides for preventing or treating a disease by administering the MSCs and/or cells of the adipocyte lineage described herein in a prophylactically or therapeutically effective amount for the prevention or treatment of diseases in animals, both human and non-human.

Typically, in the prophylaxis or treatment of disease states, the recipient is most preferably only required to undergo a single administration after which immunization or disease emission, respectively are realized on a permanent basis. Alternatively, boosters can be administered at intervals which can be determined by conventional studies using protocols known to those of ordinary skill in the art. Alternatively, in the case of therapeutic use, readministration would normally be the result of regular examinations during which the return of clinical symptoms is observed, for example, in the case of infection with HIV-1, patients are regularly monitored for elevations in "viral loading" which can indicate the imminent onset of clinical AIDS symptoms. Further, for example, solid or circulating tumors are regularly monitored for their mass or cell population or the lack of remission or advance in clinical stage (i.e. mass of solid tumor). Further, serology or other body sample testing can be performed on a regular basis to determine an increase in antigen or organism of a previously acquired infection.

Whether a single administration or multi-administration is required, it is customary to administer from about 0.5 to about 5 million cells per kilogram of recipient body weight. Depending upon observation of follow-up monitoring, any subsequent administration may be of greater or lesser dose. Such procedures and monitoring regimens are well known to those who are versed in the field of infectious disease, oncology, epidemiology and the like. The vaccine in addition to the cells may include a pharmaceutically acceptable carrier of a type known in the art and may include other components; for example, an adjuvant.

The vaccine may be administered by procedures known in the art; e.g., intramuscular, intravenous, etc. and such procedures are deemed to be within the skill in the art from the teachings herein.

The following examples further illustrate experiments which have demonstrated reduction to practice and utility of selected preferred embodiments of the present invention, although they are in no way a limitation of the teachings or disclosure of the present invention as set forth herein.

EXAMPLE 1

Tetanus Antigen Presentation by hMSCs

The principles of this invention are demonstrated by experiments using unmodified and B7-1/B7-2 transduced MSCs, co-cultured with $CD4^+$ tetanus toxoid enriched T-lymphocytes (Tet-T).

Human MSCs were evaluated for expression of MHC class II molecules and the co-stimulatory molecules, B7-1 and B7-2, to determine whether they were capable of antigen presentation resulting in activation of $CD4^+$ T cells. Evaluation by immunofluorescence staining showed that hMSCs did not express any of these molecules on their surface; however, after induction with IFN-γ, hMSCs expressed cell surface class II molecules, but not B7-1 nor B7-2. hMSCs from two individuals were evaluated for their ability to present tetanus toxoid to autologous $CD4^+$ T cell lines specific for this antigen. There was little or no stimulation of the T cell lines, as measured by lymphoproliferation, regardless of IFN-γ treatment. All of these results were confirmed by RT-PCR studies (data not shown).

Figure 1:
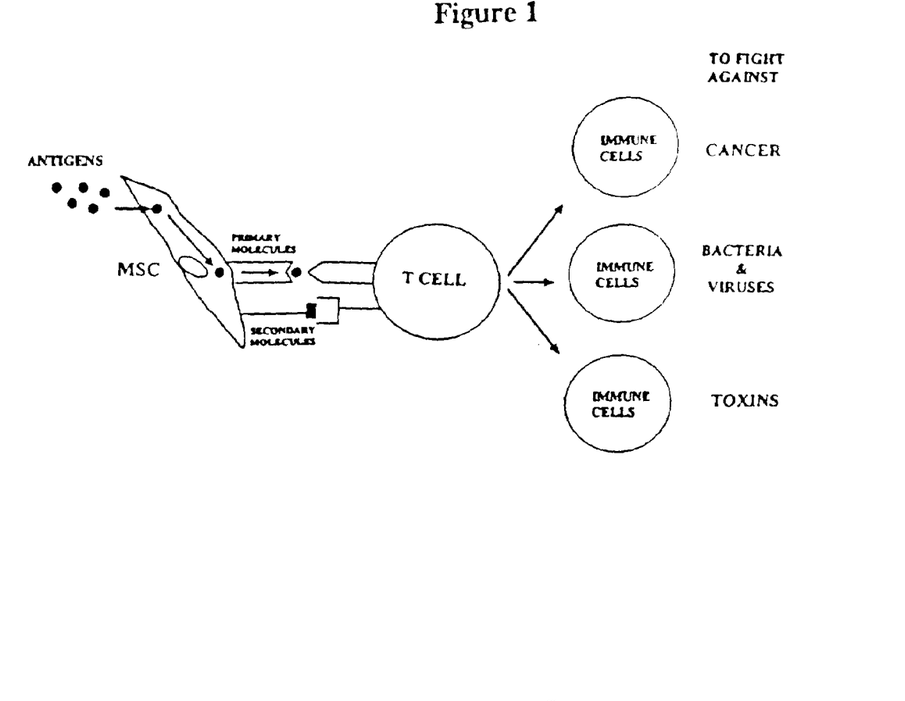
FIG. 1 is an illustration of the cell-to-cell interaction of antigen stimulated mesenchymal stem cells that serve as antigen presenting cells to dormant T-cell populations and which results in their activation to perform the various T-cell immune response roles, including activation of other immune response cell systems.
Figure 2:
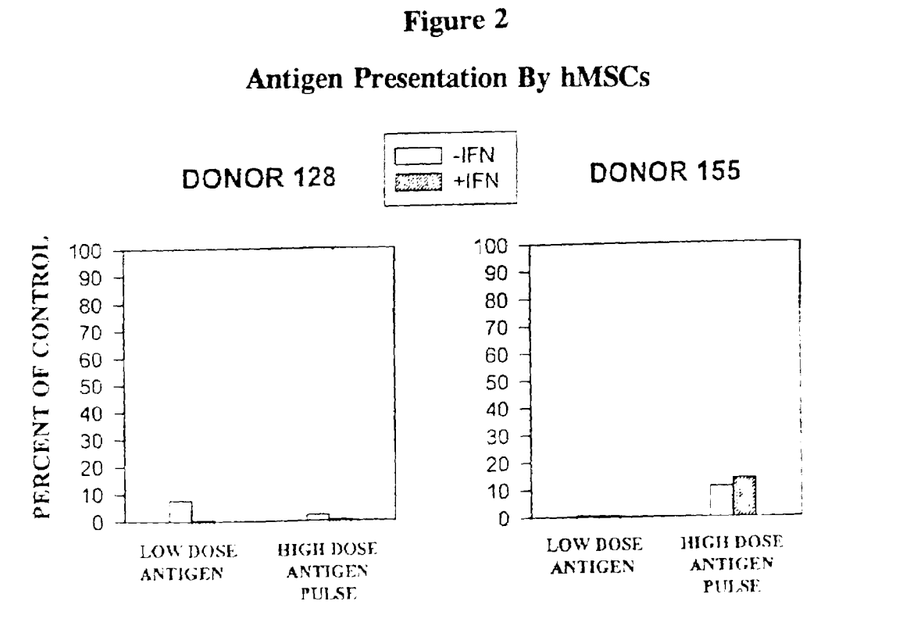
FIG. 2 shows that when hMSCs were substituted as APCs, there was minimal activation of the $T_{TET}$ line from either donor, whether or not the hMSCs were pre-treated with IFN-γ.
Figure 3:
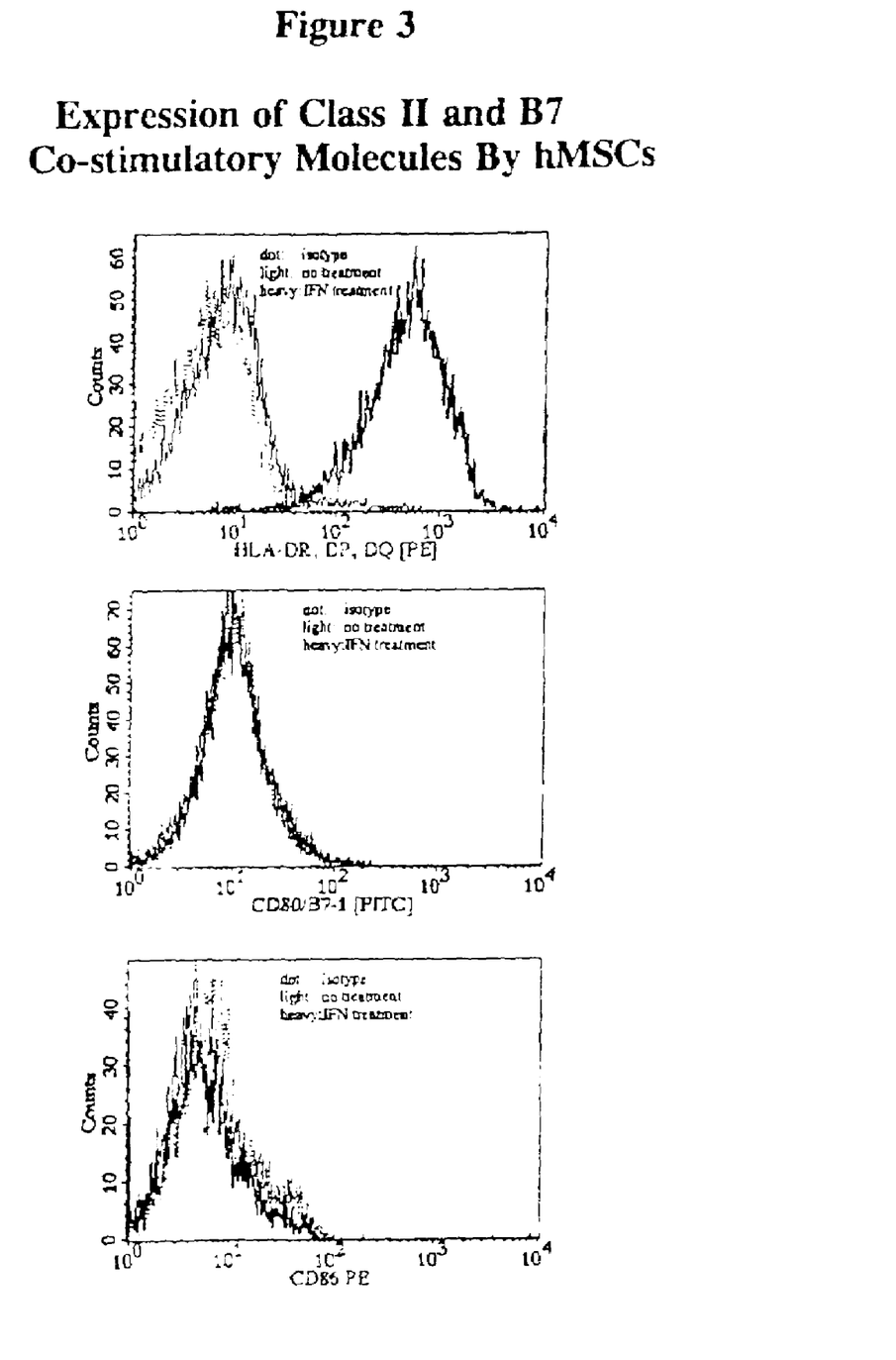
FIG. 3 shows that treatment with IFN-γ increased HLA II expression, but did not increase B7-1 expression nor B7-2 (CD 86) expression in non-transduced hMSCs.

The induction of class II expression by IFN-γ indicated that hMSCs may present antigen to CD4⁺ T cells. To test this, bone marrow and peripheral blood mononuclear cells were obtained from 2 donors, #128 and #155. hMSCs were expanded from the bone marrow cells, and tetanus toxoid T cell lines ($T_{TET}$) were produced from PBMCs by stimulation with soluble tetanus toxoid followed by expansion of the activated T cells with IL-2. The expanded cells were depleted of APCs by labeling B cells and monocytes with magnetic particles and removing them in a magnetic field. Thus, the tetanus toxoid T cell lines were unable to respond to tetanus toxoid unless APCs were added. Addition of irradiated PBMC containing professional APCs (monocytes and dendritic cells) plus soluble tetanus toxoid resulted in the activation and proliferation of the T cell line which was assessed by uptake of $^3$H-thymidine. When hMSCs were substituted as APCs, there was minimal activation of the $T_{TET}$ line from either donor, whether or not the hMSCs were pre-treated with IFN-γ (FIG. 2). To rule out lack of presentation due to inefficient uptake and processing of antigen, hMSCs were pulsed with a high concentration of tetanus toxoid (100 μg/ml) for 24 hrs prior to co-culture with the $T_{TET}$ lines, rather than the typical low dose of toxoid found to be optimal for PBMC presentation (1 μg/ml). This resulted in a small, but noticeable increase in T cell activation (approximately 10% of the response of control cultures containing professional APCs).

The relatively low level of antigen presentation by hMSCs may have been due to inadequate numbers of co-stimulatory molecules on the cell surface. Therefore, the hMSCs were engineered to express B7 co-stimulatory molecules. B7-1 and B7-2 molecules were cloned from human bone marrow and inserted into replication-deficient murine Moloney Leukemia Virus (MuLV) containing the neomycin selection marker. The sequences of B7-1 and B7-2 are available from the GenBank sequence database (National Center for Biotechnology Information, Bethesda, Md.) as Accession Nos. V04343 and L25259, respectively. The retrovirus was grown by the ping-pong technique (see, e.g. Hoatlin ME et al. *J. Mol. Med.* 73(3): 113–120 (1995)), using amphotrophic and heterotrophic packaging cell lines. High titers of virus were used to transduce hMSCs from donors 128 and 155 with either B7-1 or B7-2. The cells were selected with neomycin and analyzed by immunofluorescence for cell surface expression of the transferred gene.

Figure 4:
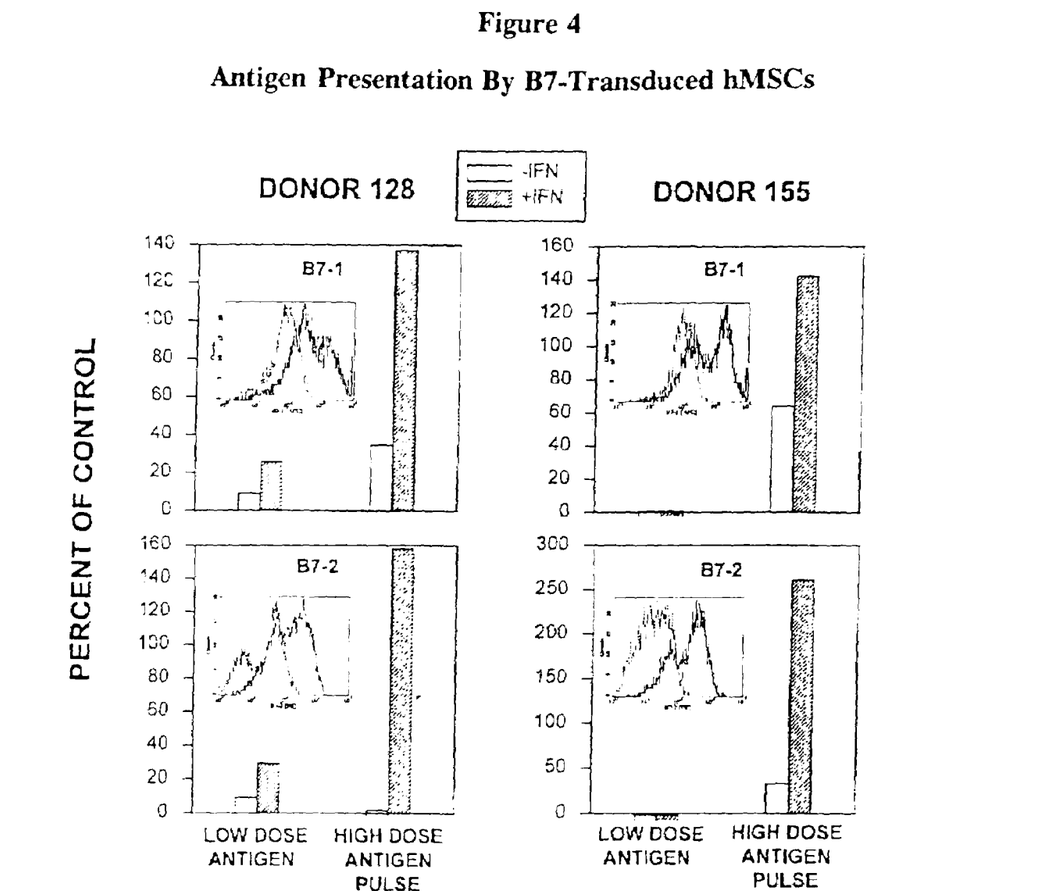
FIG. 4 shows that, in transduced hMSCs, both B7-1 and B7-2 were expressed at high levels on hMSCs of both donors (FACS analysis insets). These transduced hMSCs were analyzed for antigen presentation as described above, either untreated or pre-treated for 3 days with IFN-γ prior to co-culture with the T$_{TET}$ line and tetanus toxoid.

As shown in FIG. 4 (FACS analysis insets), both B7-1 and B7-2 were expressed at high levels on hMSCs of both donors. These transduced hMSCs were analyzed for antigen presentation as described above, either untreated or pre-treated for 3 days with IFN-γ prior to co-culture with the $T_{TET}$ line and tetanus toxoid. The antigen was administered as continuous low dose or as a 24 hr high dose pulse as described previously. Most notably, the cultures containing B7-1 or B7-2 transduced hMSCs, that were treated with IFN-γ and a high dose antigen pulse, all stimulated the $T_{TET}$ line to a greater degree than professional APCs. This effect was consistent for both donors. Most striking, donor 155 hMSCs transduced with B7-2 induced a T cell response that was 2.5 times higher than the control response. In all cases, treatment with IFN-γ significantly enhanced antigen presentation, by up-regulating class II molecules. The importance of pulsing the hMSCs with a high dose of antigen was demonstrated in both donors by the relatively low T cell responses resulting from administration of low dose antigen. The best T cell responses were from cultures containing IFN-γ treated hMSCs from donor 128, who responded 20–30% better than the control cultures containing professional APCs.

Thus, transduction of the hMSCs with B7-1 or B7-2 greatly enhanced the ability of these cells to activate the T cell lines but only if they were pretreated with IFN-γ. Full antigen presentation ability, comparable to that observed for professional APCs, was achieved by pulsing hMSCs with high concentrations of tetanus toxoid prior to coculture with the T cell line. Therefore, the combination of IFN-γ treatment, transduction of B7 molecules, and high antigen pulse renders hMSCs as fully competent APCs for CD4⁺ T cells.

EXAMPLE 2

Expression of Class II MHC Molecules by Adipocytes

Post confluent hMSCs were differentiated with adipocyte differentiation medium (MDI+I) containing DMEM-High glucose/10% FBS, insulin 10 μg/ml, antibiotic/antimycotic, dexamethasone $10^{-6}$ M, methylisobutylxanthine (MIX) 0.5 mM, and indomethacin 200 μM. The cells were treated with MDI+I for 3 days, and adipocyte maintenance medium (AM) containing DMEM-High glucose/10% FBS, 10 μg/ml insulin and an antibiotic/antimycotic for 1 day (1 cycle) for 1 to 3 cycles. Control cells (undifferentiated MSCs) were treated with hMSC medium (described in U.S. Pat. No. 5,486,359) or AM. The cells were treated with 50 U/ml of IFN-γ for 3 days and Class II MHC expression was measured at different times during adipogenesis. The cells were trypsinized and incubated with anti-human DR, DP, DQ-FITC conjugated antibody or matching isotype, and the median fluorescence intensity was measured by FACS analysis. The value for isotype control is given in parenthesis. The results are given in Table I below.

TABLE I

Expression of Class II MHC Molecules by MSCs Differentiated into Adipocytes

| | Class II expression, Median fluorescence intensity (isotype) | |
|---|---|---|
| Days after removal of IFN | Undiff. MSC | Adipo-MSCs |
| 0 | 74 (5) | 126 (3) |
| 3 | 60 (4) | 96 (2) |
| 7 | 91 (10) | 89 (8) |
| 10 | 125 (16) | 77 (14) |
| 14 | 50 (12) | 43 (13) |
| 17 | 22 (9) | 18 (8) |

Figure 5:
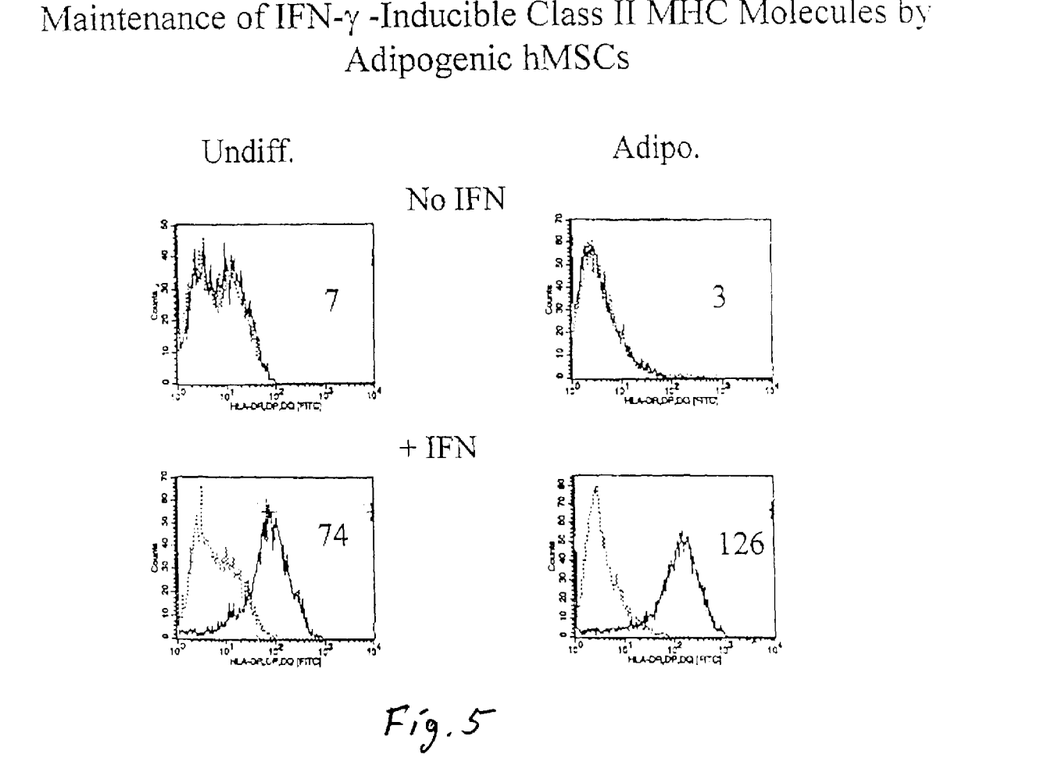
FIG. 5 shows FACS analyses of expression of class II MHC molecules by adipocytes.

FIG. 5 also indicates a greater median fluorescence intensity (MFI) of staining for Class II on the IFN treated adipocytes than on the IFN treated undifferentiated MSCs.

EXAMPLE 3

Antigen Presentation by Adipocytes

Materials and Methods.

hMSCs transduced with human B7-1 (Donor 128-B7-1) were differentiated in T175 flasks. After adipogenesis, the cells were trypsinized and counted. 1×10⁴ MSCs (undifferentiated treated with MSC medium) were plated into 96 well plates and then the T-cell proliferation assay was performed.

Tetanus toxoid (TT) (Accurate Chemical & Scientific Corp. Westbury, N.Y.) was added to final concentrations of 100, 20, 4 or µ/ml.

All cultures were washed 5× with hMSC medium (last time in T cell medium) and donor-matched TT-specific T cells were added. TT-specific T cells were thawed from liquid $N_2$, washed 1× in hMSC medium and 1× in T cell medium (IMDM, 5% Human AB serum, non-essential amino acids, sodium pyruvate, beta mercaptoethanol and penicillin, streptomycin, amphotericin mix (Gibco BRL, Frederick, Md.). $4.5 \times 10^5$ T cells were added in 1.15 ml. Controls included Undifferentiated or adipo-MSCs alone, or +T cells, no Ag. PBMCs alone or PBMCs+T cell, no Ag.

Two days after addition of T cells, culture supernatants were harvested from all wells and stored at −80° C. until analysis of IL-2, IL-4, IL-10 and IFN-γ. Fresh T cell medium was added (1 ml) and 250 µl of medium containing 5 µCi of $^3$H-Thymidine was added. The cultures were incubated at 37° C., 5% $CO_2$ for 16–18 hours. The cells were harvested and counted.

Figure 6:
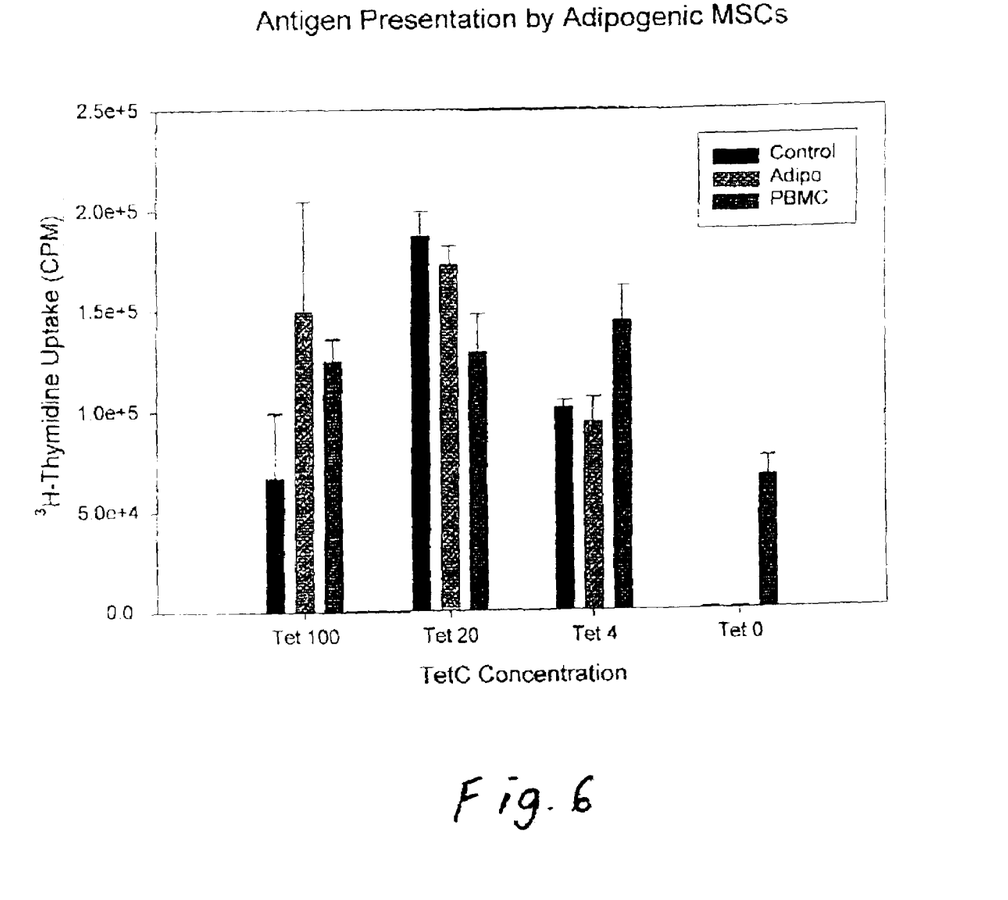
FIG. 6 shows T cell proliferation induction by adipocytes.

Results: MSCs and adipocytes equaled or exceeded the proliferation inducing activity of PBMCs. See FIG. 6.

EXAMPLE 4

Figure 7:
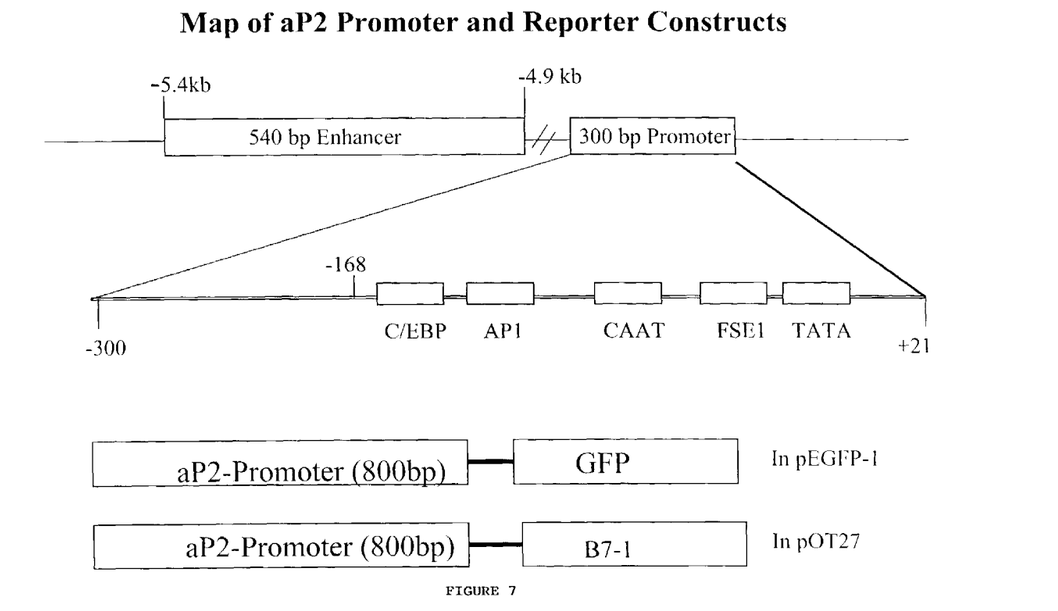
FIG. 7 shows the map of the aP2 promoter and reporter constructs.

The 800 bp aP2 promoter was produced from the 5.4 kb aP2 gene promoter (Graves et al. *J Cell Biochem* 49(3): 219–224 (1992)). The 250 bp promoter sequence and 540 bp enhancer sequence were removed and combined in the pEGFP-1 vector (Clontech, Palo Alto. CA) to delete the intervening 4.9 kb of the gene (aP2-GFP). The vector has a neomycin resistance cassette for selection of stably transfected cells. (See FIG. 7) The 800 bp aP2 promoter was cut out from the above plasmid and cloned into pOT-27 (PUC plasmid containing hB7-1 gene and SV40 poly A sequence) to produce aP2-B7-1. This vector does not have the neomycin resistence gene; therefore the cells were co-transduced with an additional vector (pCI-neo) constitutively expressing neomycin resistance gene for selection.

Figure 8:
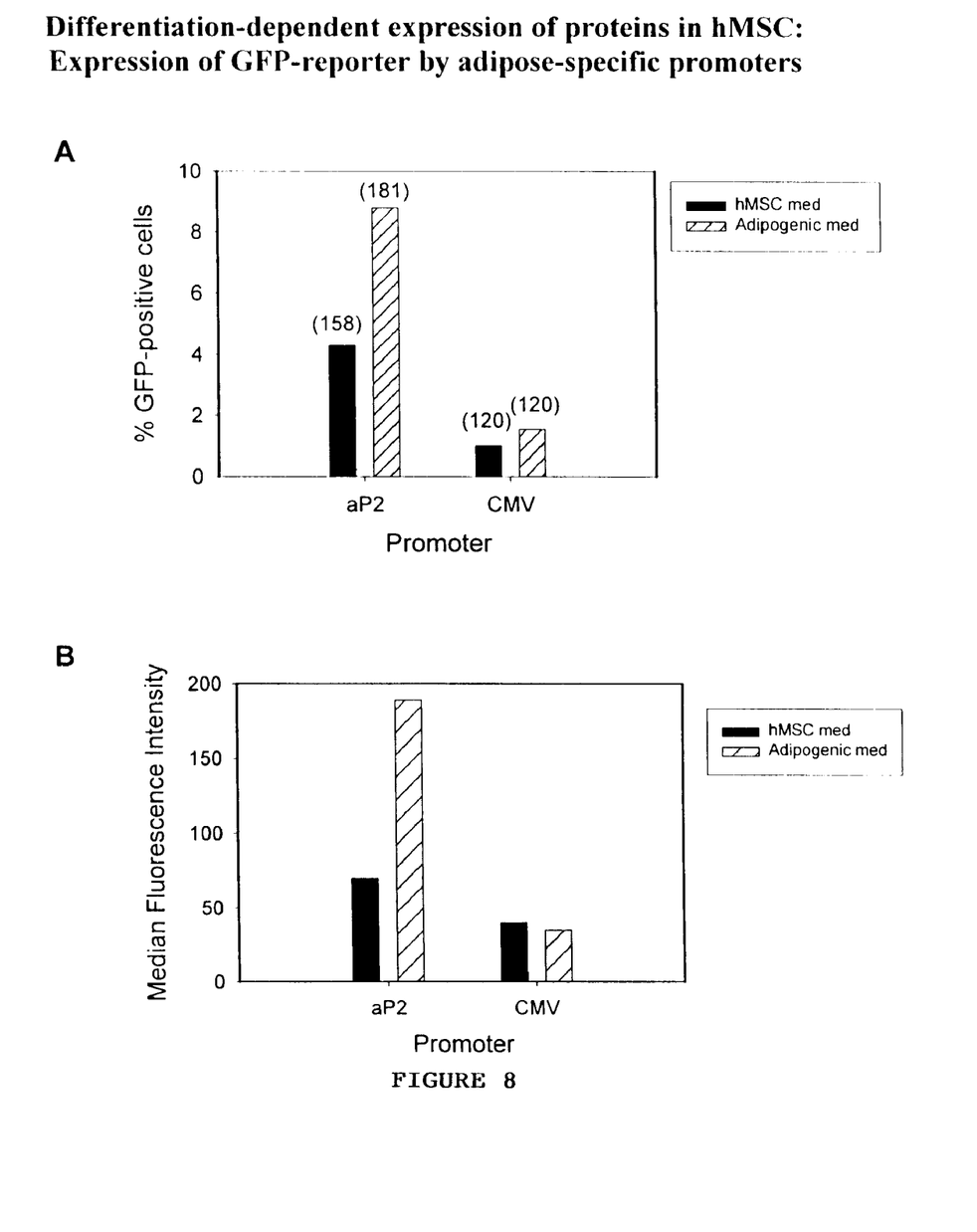
FIG. 8A and FIG. 8B show differentiation-dependent expression of proteins in hMSCs: expression of GFP-reporter by adipose-specific promoters.

EXAMPLE 5 hMSCs were transfected by electroporation with aP2-GFP and selected with G418 over a period of 2 weeks. The pEGFP-C1 vector that expresses GFP under control of the constitutive immediate early promoter of CMV was used as a control. The selected cells were plated into 6 well dishes and induced to differentiate into adipocytes for 1 or 3 cycles of adipogenesis or left undifferentiated. The expression of GFP was analyzed by FACS using non-GFP cells for background expression. FIG. 8A shows the results of GFP expression after 1 cycle of differentiation. While a 112-driven GFP increased with adipogenesis, CMV promoter-driven GFP did not change. With 3 cycles of adipogenesis more cells were GFP+ in adipogenic MSCs (photograph showing GFP expression). FACS data were not obtained.

FIG. 8B is from a different experiment performed in a similar way and shows increase in median fluorescence intensity of GFP in adipogenic cells transfected with aP2-GFP and subjected to 3 cycles of adipogenesis.

Numerous modifications and variations of the present invention are possible in light of the above teachings: therefore within the scope of the appended claims the invention may be practiced otherwise than as specifically described.

What is claimed is:

1. A composition comprising a mesenchymal stem cell that expresses at least one co-stimulatory molecule, wherein said mesenchymal stem cell has been treated with interferon-γ, and has been modified to have at least one exogenous antigen fragment bound to MHCII such that said at least one antigen is presented to initiate an immune response.

2. The composition of claim 1 wherein said mesenchymal stem cell further includes exogenous genetic material that encodes interferon-γ.

3. The composition of claim 1 wherein the co-stimulatory molecule is selected from the group consisting of B7-1 and B7-2.

4. The composition of claim 1 wherein the exogenous antigen is selected from the group consisting of a protein, a polypeptide, a glycolipid, and a lipid.

5. The composition of claim 1 wherein the mesenchymal stem cell was modified by contact with the exogenous antigen fragment or an antigen including said fragment.

6. The composition of claim 1 wherein the mesenchymal stem cell contains exogenous genetic material that encodes the exogenous antigen fragment or an antigen including said fragment.

7. The composition of claim 6 wherein said exogenous genetic material is contained in an expression vector.

8. The composition of claim 1 wherein the mesenchymal stem cell includes exogenous genetic material that encodes said at least one co-stimulatory molecule.

9. The composition of claim 8 wherein said exogenous genetic material encoding said at least one co-stimulatory molecule is contained in an expression vector.

10. A composition comprising a cell of the adipocyte lineage that expresses at least one co-stimulatory molecule, wherein said cell has been treated with interferon-γ, and has been modified to have at least one exogenous antigen fragment bound to MHC II of said cell such that said at least one antigen is presented to initiate an immune response.

11. The composition of claim 10 wherein said cell further includes exogenous genetic material that encodes interferon-γ.

12. The composition of claim 10 wherein the co-stimulatory molecule is selected from the group consisting of B7-1 and B7-2.

13. The composition of claim 10 wherein the exogenous antigen is selected from the group consisting of a protein, a polypeptide, a glycolipid, and a lipid.

14. The composition of claim 10 wherein the cell was modified by contact with the exogenous antigen fragment or an antigen including said fragment.

15. The composition of claim 10 wherein the cell contains exogenous genetic material that encodes the exogenous antigen fragment or an antigen including said fragment.

16. The composition of claim 15 wherein said exogenous genetic material is contained in an expression vector.

17. The composition of claim 10 wherein the cell includes exogenous genetic material that encodes at least one co-stimulatory molecule.

18. The composition of claim 17 wherein said exogenous genetic material encoding said at least one co-stimulatory molecule is contained in an expression vector.

* * * * *